(12) United States Patent
Ueki

(10) Patent No.: US 9,981,040 B2
(45) Date of Patent: May 29, 2018

(54) CAPSULE FORMULATION

(71) Applicant: Eisai R&D Management Co., Ltd., Tokyo (JP)

(72) Inventor: Yosuke Ueki, Gifu (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days. days.

(21) Appl. No.: 14/390,854

(22) PCT Filed: Apr. 17, 2013

(86) PCT No.: PCT/JP2013/061418
§ 371 (c)(1),
(2) Date: Oct. 6, 2014

(87) PCT Pub. No.: WO2013/157584
PCT Pub. Date: Oct. 24, 2013

(65) Prior Publication Data
US 2015/0118299 A1 Apr. 30, 2015

(30) Foreign Application Priority Data
Apr. 20, 2012 (JP) .................. 2012-097055

(51) Int. Cl.
*A61K 47/38* (2006.01)
*A61K 47/26* (2006.01)
(Continued)

(52) U.S. Cl.
CPC ............ *A61K 47/38* (2013.01); *A61K 9/4816* (2013.01); *A61K 9/4858* (2013.01);
(Continued)

(58) Field of Classification Search
CPC .... A61K 31/661; A61K 31/675; A61K 47/02; A61K 47/26; A61K 47/32; A61K 47/36;
(Continued)

(56) References Cited

U.S. PATENT DOCUMENTS

2001/0041691 A1 11/2001 Ueda et al.
2002/0119169 A1 8/2002 Angel et al.
(Continued)

FOREIGN PATENT DOCUMENTS

CN 1212832 C 8/2005
JP H08-208458 8/1996
(Continued)

OTHER PUBLICATIONS

Al-Tabakha, "HPMC Capsules: Current Status and Future Prospects," Journal of Pharmacy and Pharmaceutical Sciences 13(3) 428-442, Jan. 2010.*
(Continued)

*Primary Examiner* — Aradhana Sasan
(74) *Attorney, Agent, or Firm* — Fish & Richardson P.C.

(57) ABSTRACT

An object of the present invention is to provide a capsule formulation comprising a phosphonooxymethyl derivative of ravuconazole which suppresses delay in dissolution due to storage regardless of an encapsulated amount of the phosphonooxymethyl derivative of ravuconazole. The present invention provides a capsule formulation comprising an encapsulated material comprising {[(1R,2R)-2-[4-(4-cyanophenyl)-1,3-thiazol-2-yl]-1-(2,4-difluorophenyl)-1-(1H-1,2,4-triazol-1-ylmethyl)propyl]oxy}methyl dihydrogen phosphate or a pharmacologically acceptable salt thereof, or a solvate of any of the foregoing, and a capsule shell not comprising gelatin.

10 Claims, 2 Drawing Sheets

(51) Int. Cl.
| | |
|---|---|
| A61K 47/36 | (2006.01) |
| A61K 31/675 | (2006.01) |
| A61K 47/32 | (2006.01) |
| A61K 9/48 | (2006.01) |
| A61K 31/661 | (2006.01) |
| A61K 47/02 | (2006.01) |

(52) U.S. Cl.
CPC .......... *A61K 9/4891* (2013.01); *A61K 31/661* (2013.01); *A61K 31/675* (2013.01); *A61K 47/26* (2013.01); *A61K 47/32* (2013.01); *A61K 47/36* (2013.01); *A61K 47/02* (2013.01)

(58) Field of Classification Search
CPC .... A61K 47/38; A61K 9/4816; A61K 9/4858; A61K 9/4891
See application file for complete search history.

(56) References Cited

U.S. PATENT DOCUMENTS

| | | | |
|---|---|---|---|
| 2010/0098750 A1 | 4/2010 | Nishikawa | |
| 2010/0249426 A1* | 9/2010 | Ishimoto et al. | 548/119 |

FOREIGN PATENT DOCUMENTS

| | | |
|---|---|---|
| JP | 2001-170137 | 6/2001 |
| JP | 2003-520235 | 7/2003 |
| JP | 2008-189585 | 8/2008 |
| RU | 2266909 | 12/2005 |
| RU | 2429843 | 11/2010 |
| WO | WO 2004/047822 | 6/2004 |
| WO | WO 2007/097386 | 8/2007 |

OTHER PUBLICATIONS

Office Action issued for Russian Patent Application No. 2014140343 dated Jan. 19, 2015.
Office Action issued in Thai Application No. 1401006080, dated Oct. 29, 2015, 4 pages, with English translation.
Response to Office Action for Philippine Application No. 1-2014-502148, dated Dec. 21, 2015, 3 pages.
Office Action issued in Philippine Application No. Jan. 2014-502148, filed Jan. 27, 2016, 19 pages.
Ku, M.S. et al., Performance qualification of a new hypromellose capsule: Part I. Comparative evaluation of physical, mechanical and processability quality attributes of Vcaps Plus® and gelatin capsules, International Journal of Pharmaceutics, 386:30-41 (2010).
Extended Search Report issued in EP Application No. 13778029.2, dated Nov. 2, 2015, 6 pages.
Search Report issued in Singapore Application No. 11201406097S, dated Sep. 21, 2015, 2 pages.
Written Opinion issued in Singapore Application No. 11201406097S, dated Oct. 2, 2015, 5 pages.
Office Action issued in New Zealand Application No. 700800, dated Sep. 1, 2015, 3 pages.
Office Action issued in Philippine Application No. 1-2014-502148, dated Oct. 19, 2015, 1 page.
Bae, et al., "Film and pharmaceutical hard capsule formation properties of mungbean, waterchestnut, and sweet potato starches" Food Chem 106:96-105, 2008.
Chinese Office Action in Application No. 201380019068.8 dated Mar. 4, 2016, 7 pages, with English translation.
Chiwele et al., "The Shell Dissolution of Various Empty Hard Capsules," Chem Pharm Bull 48(7):951-956, Jul. 2000.
International Search Report in Application No. PCT/JP2013/061418, dated May 21, 2013, 4 pages, with English translation.
Japanese Pharmacopoeia 16th Edition, General Rules for Preparations, Section "1.2 Capsule," p. 10, Mar. 24, 2011, with English translation, 5 pages.
Japanese Pharmacopoeia, 16th Edition, section "6.10 Dissolution Test," pp. 117-121, Mar. 24, 2011, with English translation, 14 pages.
Takeuchi, "Strategy and novel technology on pharmaceutical preparations," 2007, pp. 73, 77 to 82, with English Translation.
Ueno et al., "Present Situation of Hard Capsules in Japan and U.S.A. Results of Questionnaires Relating with Hard Capsules in Japan," Pharm Tech Jpn, 1999, 15(7), pp. 969 to 973, with English Translation.
Office Action issued in New Zealand patent application No. 700800, dated Jan. 22, 2016, 3 pages.
Response to Chinese Office Action in Application No. 2016030100090730, dated Jul. 14, 2016, 12 pages, with English translation.
Response to Filipino Office Action in Application No. 1-2014-502148, dated May 11, 2016, 2 pages.
Taiwanese Office Action in Application No. 102113726, dated Jun. 21, 2016, 6 pages, with English translation.
Office Action issued in Chinese Application No. 201380019068.8, dated Nov. 23, 2016, 6 pages, with English translation.
Response to Office Action in counterpart Taiwanese Application No. 102113726, filed Sep. 21, 2016, 5 pages (English translation).
Office Action issued in Australian Patent Application No. 2013250251, dated Jan. 9, 2017, 3 pages, (English translation provided).
Office Action issued in Japanese Patent Application No. 2014-511237, dated Dec. 22, 2016, 6 pages, (English translation provided).
Office Action issued in Philippines Patent Application No. 1/2014/502148, dated Feb. 21, 2017, 2 pages, (English translation provided).
Modified Request for Examination for Malaysian Patent Application No. PI2014702937, filed on Mar. 30, 2017, 6 pages (English Translation).
Notice of Allowance in Australian Application No. 2013250251, dated Apr. 28, 2017, 3 pages.
Office Action issued in Chinese Application No. 201380019068.8, dated Mar. 9, 2017, 7 pages (English Translation).
Office Action issued for Russian Patent Application No. 2014140343, dated Mar. 16, 2017, 8 pages (English Translation).
Petraitiene et al., "Efficacy, Safety, and Plasma Pharmacokinetics of Escalating Dosages of Intravenously Administered Ravuconazole Lysine Phosphoester for Treatment of Experimental Pulmonary Aspergillosis in Persistently Neutropenic Rabbits," Antimicrobial Agents and Chemotherapy, 2004, 48(4):1188-1196.
Rejection issued for Japanese Patent Application No. 2014-511237, dated Mar. 9, 2017, 8 pages (English Translation).
Response to Australian Office Action in Application No. 2013250251, dated Apr. 21, 2017, 14 pages.
Response to Japanese Office Action in Application No. JP 2014-511237, dated Feb. 17, 2017, 11 pages (English Translation).
Notice of Allowance issued for Chinese Patent Application No. 201380019068.8 dated Jul. 6, 2017, 2 pages.
Notice of Allowance issued for European Patent Application No. 13778029.2 dated Nov. 24, 2016, 2 pages.
Notice of Allowance issued for Japanese Patent Application No. 2014-511237, dated Jun. 29, 2017, 5 pages (English Translation).
Notice of Allowance issued for Singapore Patent Application No. 112014060975 dated Apr. 24, 2017, 6 pages (English Translation).
Notice of Allowance issued for Taiwan Patent Application No. 102113726 dated Oct. 25, 2017, 5 pages (English Translation).
Office Action issued for Philippine Patent Application No. 1-2014-502148 dated Feb. 21, 2017, 3 pages (English Translation).
Office Action issued for Russian Patent Application No. 2014140343 dated Aug. 10, 2017, 6 pages (English Translation).
Office Action issued for Singapore Patent Application No. 11201406097S dated Sep. 21, 2016, 7 pages (English Translation).
Response to Office Action for Chinese Patent Application No. 201380019068.8 filed on Feb. 6, 2017, 30 pages (English Translation).
Response to Office Action for Chinese Patent Application No. 201380019068.8 filed on May 24, 2017, 11 pages (English Translation).

(56) References Cited

OTHER PUBLICATIONS

Response to Office Action for New Zealand Patent Application No. 700800 filed on Dec. 11, 2015, 68 pages.
Response to Office Action for New Zealand Patent Application No. 700800 filed on May 23, 2016, 2 pages (English Translation).
Response to Office Action for Philippine Patent Application No. 1-2014-502148, filed on Feb. 6, 2017, 7 pages (English Translation).
Response to Office Action for Philippine Patent Application No. 1-2014-502148, filed on Mar. 1, 2017, 3 pages (English Translation).
Response to Office Action for Russian Patent Application No. 2014140343 filed on Jun. 14, 2017, 9 pages (English Translation).
Response to Office Action for Russian Patent Application No. 2014140343 filed on Mar. 4, 2017, 6 pages (English Translation).
Response to Office Action for Thai Patent Application No. 1401006080, 3 pages.
Response to Office Action issued for Singapore Patent Application No. 11201406097S filed on Feb. 1, 2017, 3 pages (English Translation).
Response to Search Report for European Patent Application No. 13778029.2 filed on Apr. 26, 2016, 4 pages.
Decision to Grant in Russian Patent Application No. 2014140343, Nov. 14, 2017, 10 pages [English Translation].
Examination Report for Singapore Patent Application No. 112014060975, dated Apr. 24, 2017, 4 pages [English Translation].
Written Opinion in International Application No. PCT/JP2013/061418, dated May 21, 2013, 5 pages [English Translation].
Notice of Eligibility for Grant in Singapore Patent Application No. 112014060975, dated Apr. 25, 2017, 2 pages [English Translation].
Office Action in Philippine Patent Application No. 1-2014-502148, dated Feb. 21, 2017, 3 pages [English Translation].
Response in Singapore Patent Application No. 11201406097S, filed on Mar. 22, 2016, 5 pages [English Translation].
Response to Office Action in Philippine Patent Application No. 1-2014-502148, filed on Feb. 6, 2017, 34 pages [English Translation].
Response to Office Action in Philippine Patent Application No. 1-2014-502148, filed on Mar. 1, 2017, 31 pages [English Translation].
Response to Office Action in Russian Patent Application No. 2014140343, filed on Oct. 18, 2017, 6 pages [English Translation].
Response to Office Action in Russian Patent Application No. 2014140343, filed on Mar. 4, 2015, 6 pages [English Translation].
Amendment in Japanese Patent Application No. 2014-511237, dated Jun. 8, 2017, 5 pages [English Translation].
Completion of Final Requirements in Philippine Patent Application Jan. 2014-502148, dated Feb. 21, 2017, 3 pages [English Translation].
Notice of Acceptance in New Zealand Patent Application 700800, dated Jun. 22, 2016, 1 page.
Office Action in Russian Patent Application No. 2014140343, dated Jul. 11, 2017, 6 pages [English Translation].
Response to Office Action in Russian Patent Application No. 2014140343, dated Mar. 4, 2015, 9 pages [English Translation].
Subsequent Substantive Examination Report in Philippine Patent Application No. 1-2014-502148, dated Jan. 11, 2017, 4 pages.
Written Appeal in Japanese Patent Application No. 2014-511237, dated Jun. 8, 2017, 18 pages [English Translation].

* cited by examiner

CAPSULE FORMULATION

TECHNICAL FIELD

The present invention relates to a capsule formulation. Specifically, the present invention relates to a capsule formulation comprising a phosphonooxymethyl derivative of ravuconazole.

BACKGROUND ART

As dosage form for orally administered medicines, a capsule formulation comprising a capsule shell and a material encapsulated in the capsule (encapsulated material) is widely used. The most frequently used capsule shell base for forming a capsule shell is gelatin. However, a formulation produced with a capsule shell comprising gelatin as a capsule shell base (gelatin capsule shell) may cause delay in dissolution of a drug out of the capsule shell because an encapsulated material may interact with gelatin during storage.

Orally administered medicines are ingested and then allow dissolution of a drug from a formulation and the drug is then absorbed through the gastrointestinal tract to exhibit the pharmacological effects. Therefore, a formulation which has delayed dissolution due to storage generally shows decreased absorption of a drug through the gastrointestinal tract and does not provide sufficient pharmacological effects.

As a compound which generally interacts with gelatin, a compound having a carbonyl group or an aldehyde group, reducing sugars and a compound which produces aldehyde during storage are known. Specific examples thereof include lactose and polyethylene glycol (macrogol).

However, dissolution may not always be delayed to such an extent that the pharmacological effects of medicines are affected even when a compound interacting with gelatin is encapsulated in a gelatin capsule shell. For example, medicines which comprise granules comprising lactose or polyethylene glycol encapsulated in a gelatin capsule shell are widely distributed. In addition, a gelatin capsule shell comprising polyethylene glycol in the capsule shell per se is also commercially available and medicines using the capsule shell are also distributed in Japan.

Thus it is difficult to predict whether or not a medicine comprising a drug encapsulated in a gelatin capsule shell causes delay in dissolution to such an extent that the pharmacological effects may be affected.

Ravuconazole is a triazole compound having an antifungal effect and has low water solubility. Patent Document 1 discloses a phosphonooxymethyl derivative of ravuconazole which is a prodrug of ravuconazole having improved solubility. Patent Document 2 discloses a formulation comprising a phosphonooxymethyl derivative of ravuconazole. However, Patent Document 2 does not disclose dissolution behavior of the phosphonooxymethyl derivative of ravuconazole from the formulation or delay in dissolution due to storage and does not disclose the capsule shell base.

PRIOR ART DOCUMENT

Patent Document

Patent Document 1: Japanese Translation of PCT Application No. 2003-520235
Patent Document 2: WO 2007/097386

SUMMARY OF INVENTION

Problems to be Solved by the Invention

The present inventor has found that when encapsulating a phosphonooxymethyl derivative of ravuconazole in a gelatin capsule shell, dissolution of the phosphonooxymethyl derivative of ravuconazole out of the capsule shell is significantly delayed after storage. An object of the present invention is to provide a capsule formulation comprising a phosphonooxymethyl derivative of ravuconazole which suppresses delay in dissolution due to storage regardless of an encapsulated amount of the phosphonooxymethyl derivative of ravuconazole.

Means for Solving the Problem

The present invention relates to a capsule formulation in which a capsule shell not comprising gelatin is used as a capsule shell for encapsulating a phosphonooxymethyl derivative of ravuconazole.

The present invention encompasses the followings.

[1] A capsule formulation comprising
an encapsulated material comprising
{[(1R,2R)-2-[4-(4-cyanophenyl)-1,3-thiazol-2-yl]-1-(2,4-difluorophenyl)-1-(1H-1,2,4-triazol-1-ylmethyl)propyl]oxy}methyl dihydrogen phosphate (hereinafter occasionally referred to as "compound 1") or a pharmacologically acceptable salt thereof, or a solvate of any of the foregoing (in the description, collectively and occasionally referred to as "phosphonooxymethyl derivative of ravuconazole") and
a capsule shell not comprising gelatin;

[2] The capsule formulation according to the above item [1], wherein the capsule shell is formed with a capsule shell base comprising starch, pullulan, polyvinyl alcohol or hypromellose;

[3] The capsule formulation according to the above item [1], wherein the capsule shell is formed with a capsule shell base comprising pullulan or hypromellose;

[4] The capsule formulation according to the above item [1], wherein the capsule shell is formed with a capsule shell base comprising hypromellose;

[5] The capsule formulation according to any of the above items [1] to [4], wherein the phosphonooxymethyl derivative of ravuconazole is
L-lysine-{[(1R,2R)-2-[4-(4-cyanophenyl)-1,3-thiazol-2-yl]-1-(2,4-difluorophenyl)-1-(1H-1,2,4-triazol-1-ylmethyl)propyl]oxy}methyl dihydrogen phosphate-ethanol (1/1/1) (hereinafter occasionally referred to as "compound 2");

[6] The capsule formulation according to any of the above items [1] to [5], wherein the encapsulated material further comprises magnesium oxide;

[7] The capsule formulation according to any of the above items [1] to [6], wherein a mass ratio of the phosphonooxymethyl derivative of ravuconazole in terms of a mass of the compound 2 based on the capsule shell is 0.27 or more;

[8] The capsule formulation according to any of the above items [1] to [6], wherein a mass ratio of the phosphonooxymethyl derivative of ravuconazole in terms of a mass of the compound 2 based on the capsule shell is from 0.27 to 10;

[9] The capsule formulation according to the above item [7] or [8], wherein a content of the phosphonooxymethyl derivative of ravuconazole in terms of the mass of the compound 2 per capsule shell is 17 mg or more;

[10] The capsule formulation according to any of the above items [1] to [9], wherein an average dissolution rate of the phosphonooxymethyl derivative of ravuconazole at 60 minutes after initiation of the Dissolution Test according to the Japanese Pharmacopoeia 16th edition is 60% or more after the formulation is stored in an unsealed state under the conditions of 40° C. and 75% relative humidity for 1 month; and

[11] The capsule formulation according to any of the above items [1] to [9], wherein an average dissolution rate of the phosphonooxymethyl derivative of ravuconazole at 60 minutes after initiation of the Dissolution Test according to the Japanese Pharmacopoeia 16th edition is 85% or more after the formulation is stored in an unsealed state under the conditions of 40° C. and 75% relative humidity for 1 month.

Advantageous Effect

According to the present invention, a capsule formulation can be provided which can suppress delay in dissolution of a phosphonooxymethyl derivative of ravuconazole which may occur during storage, regardless of an encapsulated amount of the phosphonooxymethyl derivative of ravuconazole.

MODE FOR CARRYING OUT THE INVENTION

Figure 1:
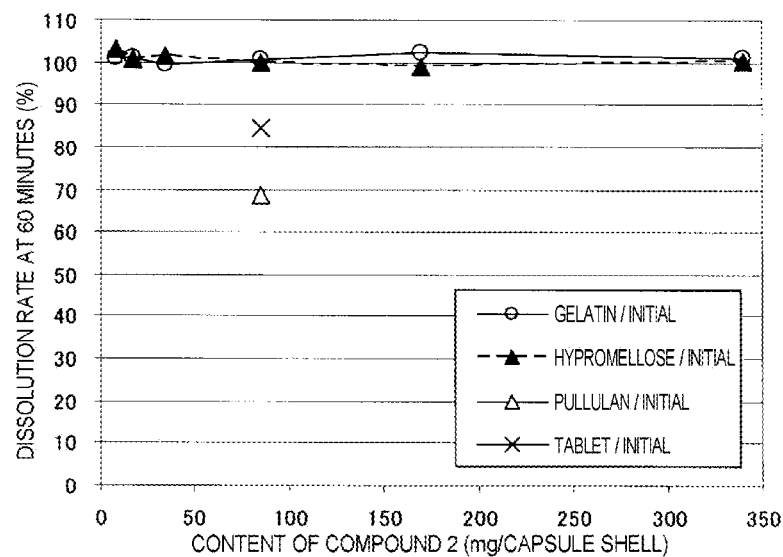
FIG. 1 is a graph in which the relationship between a content of a drug and an average dissolution rate at 60 minutes after initiation of the test (dissolution rate at 60 minutes) is compared among samples before storage, which is also described in Table 1 of Test Example 1.

The modes for carrying out the present invention are exemplified by the following embodiments. Thus the following embodiments do not limit the present invention. Embodiments modified by a person skilled in the art, for example, are also encompassed within the scope of the present invention as far as they are in conformity with the idea of the present invention.

(Capsule Formulation)

The present invention is a capsule formulation comprising an encapsulated material comprising a phosphonooxymethyl derivative of ravuconazole, and a capsule shell not comprising gelatin. In the present invention, the phosphonooxymethyl derivative of ravuconazole is encapsulated in the capsule shell not comprising gelatin.

(Phosphonooxymethyl Derivative of Ravuconazole)

In the present invention, the phosphonooxymethyl derivative of ravuconazole is {[(1R,2R)-2-[4-(4-cyanophenyl)-1,3-thiazol-2-yl]-1-(2,4-difluorophenyl)-1-(1H-1,2,4-triazol-1-ylmethyl)propyl]oxy}methyl dihydrogen phosphate (compound 1) or a pharmacologically acceptable salt thereof. The phosphonooxymethyl derivative of ravuconazole may also be a solvate of compound 1 or a pharmacologically acceptable salt thereof. Examples of the solvate include, a hydrate and an ethanolate.

Examples of a pharmacologically acceptable salt of compound 1 include a salt with an inorganic base, a salt with an organic base and a salt with a basic amino acid.

Examples of a salt with an inorganic base include an alkali metal salt such as a sodium salt, a potassium salt and the like; an alkaline earth metal salt such as a calcium salt, a magnesium salt and the like; and an ammonium salt.

Examples of a salt with an organic base include a salt with an alkyl amine such as trimethylamine, triethylamine and the like; an alkanolamine such as ethanolamine, diethanolamine, triethanolamine and the like; a heterocyclic amine such as pyridine, picoline and the like; dicyclohexylamine; and N,N'-dibenzyl ethylenediamine.

An example of a salt with a basic amino acid includes a salt with lysine, ornithine, histidine or arginine. A salt with a basic amino acid is preferably a mono-, di- or tri-salt with a basic amino acid.

A pharmacologically acceptable salt is preferably a salt with lysine, more preferably a salt with L-lysine and still more preferably a mono-L-lysine salt (L-lysine salt; mono-lysine salt) or a di-L-lysine salt (di-lysine salt).

A phosphonooxymethyl derivative of ravuconazole is preferably a solvate of a pharmacologically acceptable salt thereof. The solvate is preferably an ethanolate of a mono-L-lysine salt or an ethanolate of a di-L-lysine salt and more preferably L-lysine-{[(1R,2R)-2-[4-(4-cyanophenyl)-1,3-thiazol-2-yl]-1-(2,4-difluorophenyl)-1-(1H-1,2,4-triazol-1-ylmethyl)propyl]oxy}methyl dihydrogen phosphate-ethanol (1/1/1) (compound 2).

Compound 1 is a compound represented by the following formula 1 and compound 2 is a compound represented by the following formula 2:

Formula 1

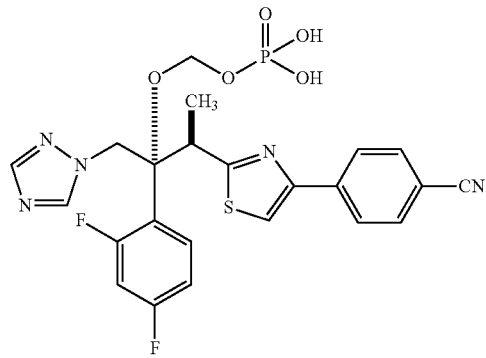

-continued

Formula 2

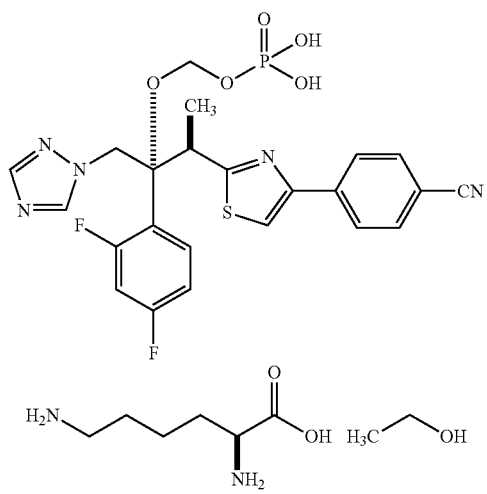

Compounds 1 and 2 encompassed in a phosphonooxymethyl derivative of ravuconazole can be produced according to the description of Japanese Translation of PCT Application No. 2003-520235 (Patent Document 1) and WO 2007/097386 (Patent Document 2).

(Capsule Shell not Comprising Gelatin)

In the present invention, the term "capsule shell not comprising gelatin" means a capsule shell that does not comprise gelatin as a capsule shell base which is a main component of the capsule shell. An example of the capsule shell includes a capsule shell comprising, for example, hypromellose, pullulan, polyvinyl alcohol or starch as a capsule shell base. The capsule shell is preferably a capsule shell comprising hypromellose or pullulan as a capsule shell base and more preferably a capsule shell comprising hypromellose as a capsule shell base. The capsule shell may also comprise, in addition to the capsule shell base such as hypromellose, pullulan, polyvinyl alcohol, starch and the like, a gelation agent such as carageenan; an auxiliary gelation agent such as potassium chloride; a colorant; and other components that may be usually added to a capsule shell, as a component of a capsule shell. As a capsule shell comprising hypromellose or pullulan as a capsule shell base, for example, a commercially available product can be used. A capsule shell comprising polyvinyl alcohol as a capsule shell base can be produced according to, for example, the method described in Patent Publication JP-A-2001-170137 and a capsule shell comprising starch as a capsule shell base can be produced according to, for example, the method described in Ho J. Bae, et al. "Film and pharmaceutical hard capsule formation properties of mungbean, water chestnut, and sweet potato starches", Food Chemistry, 106 (2008) p. 96-105.

(Encapsulated Material)

In the present invention, the term "an encapsulated material" means a content which is present in (inside of) a capsule shell in the case of being present as a capsule formulation and not the capsule shell per se or a component thereof.

An encapsulated material is not particularly limited as far as it comprises a phosphonooxymethyl derivative of ravuconazole and may be a composition comprising a phosphonooxymethyl derivative of ravuconazole.

An example of the composition comprising a phosphonooxymethyl derivative of ravuconazole includes a composition which comprises a phosphonooxymethyl derivative of ravuconazole and optionally a pharmacologically acceptable additive such as a stabilizer, an excipient, a binder, a disintegrating agent, a lubricant, an antioxidant, a flavoring agent, a colorant and a fragrance. Examples of the composition include a composition obtained by mixing a phosphonooxymethyl derivative of ravuconazole with the above additive; a granulated composition produced by adding to a phosphonooxymethyl derivative of ravuconazole the above additive and subjecting to any granulation such as agitation granulation, extrusion granulation, tumbling granulation, fluidized-bed granulation, spray granulation and the like (in case of the composition, the above additive may comprise a solvent); and a composition comprising the above granules mixed with the above additive.

In the present invention, it is preferable that an encapsulated material does not comprise gelatin.

Examples of a stabilizer include various basic substances disclosed in WO 2007/097386 (Patent Document 2). Two or more basic substances may be used in combination.

A basic substance may be a substance having pH 7 or more in the form of a 1% aqueous solution or suspension, preferably a substance having pH 8 or more in the form of a 1% aqueous solution or suspension and more preferably a substance having pH 10 or more in the form of a 1% aqueous solution or suspension. Examples of a basic substance include an inorganic base, an organic base, a basic amino acid and a basic polymer.

Examples of an inorganic base include magnesium carbonate hydroxide, potassium hydrogen carbonate, sodium hydrogen carbonate, potassium carbonate, sodium carbonate, magnesium carbonate, calcium carbonate, barium carbonate, heavy magnesium carbonate, precipitated calcium carbonate, lithium hydroxide, potassium hydroxide, sodium hydroxide, magnesium hydroxide, calcium hydroxide, magnesium-alumina hydroxide, dried aluminum hydroxide gel, magnesium oxide, calcium oxide, barium oxide, calcium silicate, magnesium silicate, magnesium aluminum silicate, magnesium aluminate, magnesium metasilicate-aluminate, sodium hydrogen phosphate, sodium dihydrogen phosphate, synthetic hydrotalcite, a co-precipitate of aluminum hydroxide and magnesium hydroxide, a co-precipitate of aluminum hydroxide, magnesium carbonate and calcium carbonate and a co-precipitate of aluminum hydroxide and sodium hydrogen carbonate. An inorganic base is preferably magnesium carbonate hydroxide, magnesium oxide, magnesium hydroxide, sodium carbonate, calcium carbonate, sodium hydrogen carbonate or calcium silicate and more preferably magnesium carbonate hydroxide, magnesium hydroxide, magnesium oxide or sodium hydrogen carbonate.

Examples of an organic base include calcium stearate, magnesium stearate, sodium stearate, sodium stearyl fumarate, trisodium citrate, sodium benzoate, monoethanolamine, diethanolamine, triethanolamine, tributylamine, dicyclohexylmethylamine and N-methylpyrrolidine. An organic base is preferably calcium stearate, trisodium citrate or sodium benzoate and more preferably sodium benzoate.

Examples of a basic amino acid include lysine, ornithine, histidine and arginine. A basic amino acid is preferably lysine or arginine and more preferably arginine.

Examples of a basic polymer include, for example, aminoalkyl methacrylate copolymer E, polyvinylacetal diethylaminoacetate and ethylcellulose.

A basic substance is preferably magnesium carbonate hydroxide, magnesium hydroxide, magnesium oxide, sodium hydrogen carbonate or arginine and more preferably magnesium oxide.

Examples of an excipient include lactose, sucrose, glucose, fructose, starch, potato starch, corn starch, wheat starch, rice starch, crystalline cellulose, microcrystalline cellulose, powdered glycyrrhiza, mannitol, erythritol, maltitol, sorbitol, trehalose, anhydrous silicic acid, calcium silicate, sodium hydrogen carbonate, calcium phosphate, anhydrous calcium phosphate and calcium sulfate.

Examples of a binder include starch, acacia, tragacanth, carboxymethyl cellulose, hydroxypropyl cellulose, hydroxypropyl methylcellulose, polyvinylpyrrolidone, methylcellulose, partly pregelatinized starch, pregelatinized starch, polyvinyl alcohol, sodium alginate, pullulan and glycerine.

Examples of a disintegrating agent include an amino acid, starch, corn starch, calcium carbonate, carmellose, carmellose calcium, croscarmellose sodium, low substituted hydroxypropyl cellulose, hydroxypropyl starch and crospovidone.

Examples of a lubricant include magnesium stearate, stearic acid, calcium stearate, sodium stearyl fumarate, talc and macrogol.

Examples of an antioxidant include sodium ascorbate, L-cysteine, sodium sulfite, tocopherol and soy lecithin.

Examples of a flavoring agent include citric acid, ascorbic acid, tartaric acid, malic acid, aspartame, acesulfame potassium, thaumatin, sucralose, saccharin sodium, dipotassium glycyrrhizinate, sodium glutamate, sodium 5'-inosinate and sodium 5'-guanylate.

Examples of a colorant include titanium oxide, iron sesquioxide, yellow iron sesquioxide, cochineal, carmine, riboflavin, Food yellow No. 5 and Food blue No. 2.

Examples of a flavoring agent include lemon oil, orange oil, menthol, peppermint oil, borneol and vanilla flavor.

In the capsule formulation of the present invention, a mass ratio of the phosphonooxymethyl derivative of ravuconazole based on the capsule shell (phosphonooxymethyl derivative of ravuconazole/capsule shell) is, when it is calculated based on a mass in terms of compound 2, generally 0.10 or more, preferably 0.27 or more, more preferably 0.53 or more and still more preferably 1.3 or more. The term "a mass in terms of compound 2" is the value obtained by converting a mass of an encapsulated phosphonooxymethyl derivative of ravuconazole to a mass of an equimolar compound 2 using the ratio in molecular weight of compound 2 and the encapsulated phosphonooxymethyl derivative of ravuconazole.

The upper limit of the mass ratio of the phosphonooxymethyl derivative of ravuconazole based on the capsule shell is determined according to the mass and inner volume of the capsule shell. The mass ratio of the phosphonooxymethyl derivative of ravuconazole based on the capsule shell is, when it is calculated based on the mass in terms of compound 2, generally 10 or less, preferably 5.0 or less, more preferably 4.5 or less and still more preferably 4.0 or less.

The mass ratio of the phosphonooxymethyl derivative of ravuconazole based on the capsule shell (when it is calculated based on the mass in terms of compound 2; the same applies hereinafter in this paragraph) is generally 0.10 to 10, preferably 0.27 to 10, more preferably 0.53 to 10 and still more preferably 1.3 to 10; when the upper limit of the mass ratio of the phosphonooxymethyl derivative of ravuconazole based on the capsule shell is 5.0, it is generally 0.10 to 5.0, preferably 0.27 to 5.0, more preferably 0.53 to 5.0 and still more preferably 1.3 to 5.0.

In the capsule formulation of the present invention, a content of the phosphonooxymethyl derivative of ravuconazole per capsule shell is, in terms of a mass of compound 2, preferably 5 mg or more, preferably 17 mg or more, more preferably 34 mg or more and still more preferably 85 mg or more. The term "a mass in terms of compound 2" is the value obtained by converting a mass of an encapsulated phosphonooxymethyl derivative of ravuconazole to a mass of an equimolar compound 2 using the ratio in molecular weight of compound 2 and the encapsulated phosphonooxymethyl derivative of ravuconazole.

In the capsule formulation of the present invention, generally a mass ratio of the phosphonooxymethyl derivative of ravuconazole (in terms of a mass of compound 2; the same applies hereinafter in this paragraph) based on the capsule shell is 0.10 to 10 and a content of the phosphonooxymethyl derivative of ravuconazole per capsule shell is 5 mg or more, preferably the mass ratio of the phosphonooxymethyl derivative of ravuconazole based on the capsule shell is 0.27 to 10 and the content of the phosphonooxymethyl derivative of ravuconazole per capsule shell is 17 mg or more, more preferably the mass ratio of the phosphonooxymethyl derivative of ravuconazole based on the capsule shell is 0.53 to 10 and the content of the phosphonooxymethyl derivative of ravuconazole per capsule shell is 34 mg or more and still more preferably the mass ratio of the phosphonooxymethyl derivative of ravuconazole based on the capsule shell is 1.3 to 10 and the content of the phosphonooxymethyl derivative of ravuconazole per capsule shell is 85 mg or more.

The upper limit of the content of the phosphonooxymethyl derivative of ravuconazole per capsule shell is generally determined according to the inner volume of the capsule shell used although it may vary depending on a dose that is required for provision of the desired pharmacological effect. The content of the phosphonooxymethyl derivative of ravuconazole per capsule shell based on the inner volume of the capsule shell is generally 1.5 g/mL or less, preferably 0.8 g/mL or less and more preferably 0.7 g/mL or less.

In the present invention, although the content rate of the phosphonooxymethyl derivative of ravuconazole in the encapsulated material is not particularly limited, the content rate is preferably high in view of taking a medicine, so that the size of the formulation can be reduced. The capsule formulation of the present invention can, even if a content rate of the phosphonooxymethyl derivative of ravuconazole is high, release generally 60% or more and preferably 85% or more of the phosphonooxymethyl derivative of ravuconazole as an average dissolution rate at 60 minutes after initiation of the dissolution test after storage. In the present invention, a content rate of the phosphonooxymethyl derivative of ravuconazole based on a mass of the encapsulated material is generally 50% or more, preferably 75% or more, more preferably 90% or more and still more preferably 95% or more.

(Production Method of Capsule Formulation)

The capsule formulation of the present invention can be produced according to the known methods including the method described in the section "1.2 Capsule" (page 10) of the Japanese Pharmacopoeia 16th edition, General Rules for Preparations. Examples of a method for producing the capsule formulation include a method in which only the phosphonooxymethyl derivative of ravuconazole is encapsulated in the capsule shell; a method in which a composition comprising the phosphonooxymethyl derivative of ravuconazole optionally mixed with the additive such as the excipient, the binder, the disintegrating agent, the lubricant and the like is encapsulated in the capsule shell; a method in which the phosphonooxymethyl derivative of ravuconazole optionally added with the additive such as the excipient, the binder, the disintegrating agent, the solvent and the like is subjected to any granulation including agitation granulation, extrusion granulation, tumbling granulation, fluidized-bed granulation, spray granulation and the like to produce granules which are then encapsulated in the capsule; and a method in which a composition comprising the above granules optionally mixed with the additive such as the excipient, the binder, the disintegrating agent, the lubricant and the like is encapsulated in the capsule shell.

(Use of Capsule Formulation)

The capsule formulation of the present invention can be administered with the purpose of treating diseases in animals, particularly mammals, more specifically human. The indication of the capsule formulation of the present invention is not particularly limited as far as it is the disease to which the phosphonooxymethyl derivative of ravuconazole may be applied. The capsule formulation of the present invention is applicable to the treatment of mycotic infections such as candidiasis, onychomycosis and the like. The dosage of the phosphonooxymethyl derivative of ravuconazole which is the pharmacologically active substance may vary according to the various conditions including the activity of the pharmacologically active substance, the symptom, age, body weight of patients and the like. The guideline dosage for oral administration is 10 to 2000 mg/day and preferably 50 to 1000 mg/day.

The capsule formulation of the present invention can release generally 60% or more, preferably 75% or more, more preferably 85% or more, still more preferably 90% or more and particularly preferably 95% or more of the phosphonooxymethyl derivative of ravuconazole in terms of the average dissolution rate at 60 minutes after initiation of the dissolution test according to the section "6.10 Dissolution Test (pages 117 to 121)" in the Japanese Pharmacopoeia 16th edition as described in Examples, even when the formulation is stored, for example, in an unsealed state under the conditions of 40° C. and 75% relative humidity for 1 month.

The present invention is a method for suppressing delay in dissolution of the phosphonooxymethyl derivative of ravuconazole from the capsule formulation due to storage by encapsulating the encapsulated material comprising the phosphonooxymethyl derivative of ravuconazole in the capsule shell not comprising gelatin regardless of the encapsulated amount of the phosphonooxymethyl derivative of ravuconazole. An example of the storage condition includes storage in an unsealed state under the conditions of 40° C. and 75% relative humidity for 1 month.

According to the method of the present invention, the average dissolution rate of the phosphonooxymethyl derivative of ravuconazole from the capsule formulation after storage can be, for example, generally 60% or more, preferably 75% or more, more preferably 85% or more, still more preferably 90% or more and particularly preferably 95% or more.

EXAMPLES

The embodiments and effects of the present invention are hereinafter described in detail by referring to Examples and Comparative Examples. These Examples exemplify the embodiments and the present invention encompasses embodiments other than the Examples described hereinbelow. A person skilled in the art can make various modifications onto the following Examples in order to employ them as embodiments of the present invention, and the modified embodiments are also encompassed within the scope of the present invention as far as they are in conformity with the idea of the present invention.

Example 1

Compound 2 (19.88 g), a phosphonooxymethyl derivative of ravuconazole, was mixed with 0.12 g of magnesium stearate (produced by Mallinckrodt) in a vial. The resulting mixture was weighed at 8.55 mg in a hypromellose capsule shell (VcapsPlus®, size 2, produced by CAPSUGEL) to obtain a capsule formulation comprising 8.5 mg of compound 2 per capsule shell.

Example 2

Compound 2 (19.88 g), a phosphonooxymethyl derivative of ravuconazole, was mixed with 0.12 g of magnesium stearate (produced by Mallinckrodt) in a vial. The resulting mixture was weighed at 17.1 mg in a hypromellose capsule shell (VcapsPlus®, size 2, produced by CAPSUGEL) to obtain a capsule formulation comprising 17 mg of compound 2 per capsule shell.

Example 3

Compound 2 (19.88 g), a phosphonooxymethyl derivative of ravuconazole, was mixed with 0.12 g of magnesium stearate (produced by Mallinckrodt) in a vial. The resulting mixture was weighed at 34.2 mg in a hypromellose capsule shell (VcapsPlus®, size 2, produced by CAPSUGEL) to obtain a capsule formulation comprising 34 mg of compound 2 per capsule shell.

Example 4

Compound 2 (19.88 g), a phosphonooxymethyl derivative of ravuconazole, was mixed with 0.12 g of magnesium stearate (produced by Mallinckrodt) in a vial. The resulting mixture was weighed at 85.5 mg in a hypromellose capsule shell (VcapsPlus®, size 2, produced by CAPSUGEL) to obtain a capsule formulation comprising 85 mg of compound 2 per capsule shell.

Example 5

Compound 2 (19.88 g), a phosphonooxymethyl derivative of ravuconazole, was mixed with 0.12 g of magnesium stearate (produced by Mallinckrodt) in a vial. The resulting mixture was weighed at 171.0 mg in a hypromellose capsule shell (VcapsPlus®, size 2, produced by CAPSUGEL) to obtain a capsule formulation comprising 170 mg of compound 2 per capsule shell.

Example 6

Compound 2 (19.88 g), a phosphonooxymethyl derivative of ravuconazole, was mixed with 0.12 g of magnesium stearate (produced by Mallinckrodt) in a vial. The resulting mixture was weighed at 342.1 mg in a hypromellose capsule shell (VcapsPlus®, size 0, produced by CAPSUGEL) to obtain a capsule formulation comprising 340 mg of compound 2 per capsule shell.

Example 7

Compound 2 (19.88 g), a phosphonooxymethyl derivative of ravuconazole, was mixed with 0.12 g of magnesium stearate (produced by Mallinckrodt) in a vial. The resulting mixture was weighed at 85.5 mg in a pullulan capsule shell (NPcaps®, size 2, produced by CAPSUGEL) to obtain a capsule formulation comprising 85 mg of compound 2 per capsule shell.

Comparative Example 1

Compound 2 (19.88 g), a phosphonooxymethyl derivative of ravuconazole, was mixed with 0.12 g of magnesium stearate (produced by Mallinckrodt) in a vial. The resulting mixture was weighed at 8.55 mg in a gelatin capsule shell (size 2, produced by CAPSUGEL) to obtain a capsule formulation comprising 8.5 mg of compound 2 per capsule shell.

Comparative Example 2

Compound 2 (19.88 g), a phosphonooxymethyl derivative of ravuconazole, was mixed with 0.12 g of magnesium stearate (produced by Mallinckrodt) in a vial. The resulting mixture was weighed at 17.1 mg in a gelatin capsule shell (size 2, produced by CAPSUGEL) to obtain a capsule formulation comprising 17 mg of compound 2 per capsule shell.

Comparative Example 3

Compound 2 (19.88 g), a phosphonooxymethyl derivative of ravuconazole, was mixed with 0.12 g of magnesium stearate (produced by Mallinckrodt) in a vial. The resulting mixture was weighed at 34.2 mg in a gelatin capsule shell (size 2, produced by CAPSUGEL) to obtain a capsule formulation comprising 34 mg of compound 2 per capsule shell.

Comparative Example 4

Compound 2 (19.88 g), a phosphonooxymethyl derivative of ravuconazole, was mixed with 0.12 g of magnesium stearate (produced by Mallinckrodt) in a vial. The resulting mixture was weighed at 85.5 mg in a gelatin capsule shell (size 2, produced by CAPSUGEL) to obtain a capsule formulation comprising 85 mg of compound 2 per capsule shell.

Comparative Example 5

Compound 2 (19.88 g), a phosphonooxymethyl derivative of ravuconazole, was mixed with 0.12 g of magnesium stearate (produced by Mallinckrodt) in a vial. The resulting mixture was weighed at 171.0 mg in a gelatin capsule shell (size 2, produced by CAPSUGEL) to obtain a capsule formulation comprising 170 mg of compound 2 per capsule shell.

Comparative Example 6

Compound 2 (19.88 g), a phosphonooxymethyl derivative of ravuconazole, was mixed with 0.12 g of magnesium stearate (produced by Mallinckrodt) in a vial. The resulting mixture was weighed at 342.1 mg in a gelatin capsule shell (size 0, produced by CAPSUGEL) to obtain a capsule formulation comprising 340 mg of compound 2 per capsule shell.

Comparative Example 7

In a mortar, 5.0 g of compound 2, a phosphonooxymethyl derivative of ravuconazole, 0.3 g of povidone (produced by ISP), 1.5 g of croscarmellose sodium (produced by FMC International), 0.3 g of magnesium oxide (produced by Kyowa Chemical Industry Co., Ltd.) and 1.55 g of mannitol (produced by Mitsubishi Shoji Foodtech Co., Ltd.) were mixed. The resulting mixture was added with a mixture of ethanol:water=7:1 (w/w) and granulated. The granulated material was dried in a thermostatic chamber followed by particle size regulation through a sieve with mesh opening of 1 mm. The sized granules were added and mixed with 1.2 g of carmellose (produced by Nichirin Chemical Industries, Ltd.), 0.05 g of calcium silicate (produced by Tokuyama Corporation) and 0.1 g of magnesium stearate (produced by Mallinckrodt). The resulting mixture was weighed at 170 mg and compressed on a material tester (Autograph®, produced by Shimadzu Corporation) to obtain a tablet with a diameter of 7.5 mm comprising 85 mg of compound 2.

Test Example 1

The capsule formulations or the tablets obtained in Examples 1 to 7 and Comparative Examples 1 to 7 were used as samples. The samples were placed in vials and stored in an unsealed state under the conditions of 40° C. and 75% relative humidity for 1 month. The samples before and after the storage were assessed for dissolution behavior in a phosphate buffer, pH 6.8.

The dissolution test was performed according to the method described in the section "6.10 Dissolution Test" in the Japanese Pharmacopoeia 16th edition as described below. The designated vessels were respectively charged with 900 mL of the phosphate buffer, pH 6.8, and attached to an apparatus and the test solution was confirmed to be maintained at 37±0.5° C. with a thermometer which was then removed. Each of the capsule formulations was placed in the sinker depicted in FIG. 6.10-2a (page 118) of the Japanese Pharmacopoeia 16th edition and then charged into the vessels with care to exclude air bubbles from the surface of the samples. The tablets were charged into the vessels as they were with care to exclude air bubbles from the surface of the samples. Immediately after the samples were charged the apparatus was activated with a paddle rotating speed of 50 rpm and at each of the predetermined times a specimen was withdrawn from a zone midway between the surface of the test solution and the top of the rotating blade, not less than 10 mm from the vessel wall. The sampled test solution was filtered through a filter with pore size of 0.45 μm and the filtrate was used for the absorbance measurement described hereinafter. The dissolution test solution was prepared by adding to 136.1 g of potassium dihydrogen phosphate, anhydrous and 224 mL of a 2 mol/L aqueous solution of sodium hydroxide pure water up to 20 L.

The dissolution rate of compound 2 was calculated by measuring the absorbance of the test solution (filtrate) which was collected at a predetermined time and then filtered as described above and comparing the absorbance with that of the standard solution prepared separately. The absorbance was measured with a cell having an optical path length of 10 mm. The combinations of the measurement wavelength and the reference wavelength used for measurements of the samples are shown below. The following combinations also include as reference information the measurement conditions for the samples comprising less than 7 mg and of 380 mg or more of compound 2.

Figure 2:
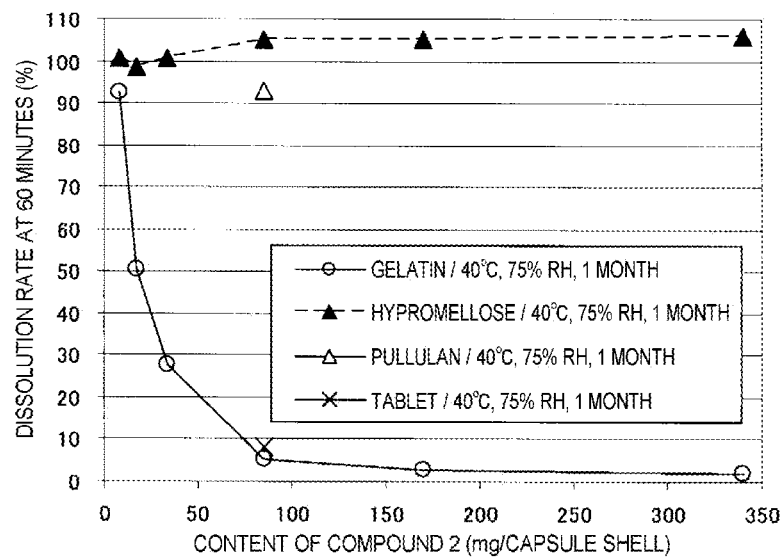
FIG. 2 is a graph in which the relationship between a content of a drug and an average dissolution rate at 60 minutes after initiation of the test (dissolution rate at 60 minutes) is compared among samples after storage for 1 month under the conditions of 40° C. and 75% relative humidity, which is also described in Table 1 of Test Example 1.
Figure 3:
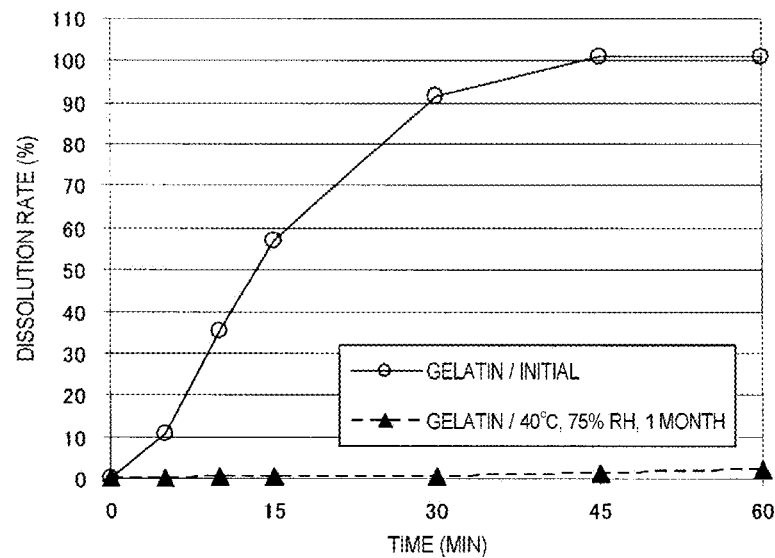
FIG. 3 is a graph in which the dissolution behavior of a drug out of a gelatin capsule shell is compared between before and after the storage for 1 month under the conditions of 40° C. and 75% relative humidity, which is also described in Table 2 of Test Example 1.
Figure 4:
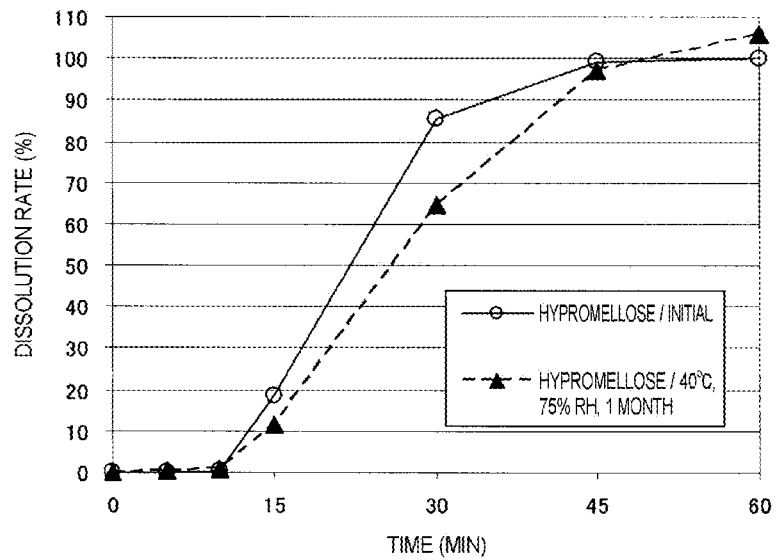
FIG. 4 is a graph in which the dissolution behavior of a drug out of a capsule shell (hypromellose capsule shell) comprising hypromellose (hydroxypropyl methylcellulose) as a base is compared between before and after the storage for 1 month under the conditions of 40° C. and 75% relative humidity, which is also described in Table 2 of Test Example 1.

Samples comprising less than 7 mg of compound 2: measurement wavelength 285 nm/reference wavelength 350 nm Samples comprising 7 mg or more and less than 40 mg of compound 2: measurement wavelength 302 nm/reference wavelength 350 nm Samples comprising 40 mg or more and less than 200 mg of compound 2: measurement wavelength 315 nm/reference wavelength 350 nm Samples comprising 200 mg or more and less than 380 mg of compound 2: measurement wavelength 318 nm/reference wavelength 350 nm Samples comprising 380 mg or more and less than 800 mg of compound 2: measurement wavelength 322 nm/reference wavelength 350 nm Samples comprising 800 mg or more of compound 2: measurement wavelength 325 nm/reference wavelength 350 nm The average dissolution rate at 60 minutes after initiation of the test (dissolution rate at 60 minutes) for the samples of Examples 1 to 7 and Comparative Examples 1 to 7 is shown in Table 1 and FIGS. 1 and 2. The profile of the dissolution rate from 5 to 60 minutes after initiation of the test for the samples of Example 6 and Comparative Example 6 is shown in Table 2 and FIGS. 3 and 4. The dissolution rate for each Examples and each Comparative Examples shown in Tables and Figures is the average dissolution rate of three samples.

With regard to the geometry change after storage, it was observed that the samples of Example 7 (pullulan capsule shell) were softened and deformed and the samples of Comparative Example 7 (tablets) were swollen. No softening or deformation of the capsule shell was observed for the samples using the hypromellose capsule shell and the gelatin capsule shell.

The average dissolution rates of the samples of Examples 1 to 7 which were stored at 40° C. did not drop compared to the initial values. Particularly, the samples of Examples 1 to 6 (hypromellose capsule shell) rapidly released 85% or more of the content of compound 2, regardless of the encapsulated amount of compound 2, at 60 minutes after initiation of the test even after the storage at 40° C. The samples of Example 7 (pullulan capsule shell) showed higher variation in the average dissolution rate among the samples compared to the samples of the hypromellose capsule shell.

It was observed that the average dissolution rates of the samples of Comparative Examples 1 to 7 after the storage at 40° C. were decreased and the extent of the drop of the average dissolution rate was more significant when the content of compound 2 was higher. Particularly, the samples of Comparative Examples 4 to 7 which comprise 85 mg or

TABLE 1

| | | EX 1 | EX 2 | EX 3 | EX 4 | EX 5 | EX 6 | EX 7 |
|---|---|---|---|---|---|---|---|---|
| Content of compound 2 (mg) | | 8.5 | 17 | 34 | 85 | 170 | 340 | 85 |
| Mass of capsule shell (mg) | | 64 | 64 | 64 | 64 | 64 | 100 | 64 |
| Mass ratio: compound 2/capsule shell | | 0.13 | 0.27 | 0.53 | 1.3 | 2.7 | 3.4 | 1.3 |
| Dissolution rate at 60 minutes (%) | Initial | 103.0 | 100.8 | 101.3 | 99.9 | 99.2 | 100.2 | 68.4 |
| | After storage in an unsealed state, 40° C. and 75% RH for 1 month | 100.8 | 98.7 | 100.4 | 105.1 | 105.2 | 106.1 | 92.7 |

| | | CE 1 | CE 2 | CE 3 | CE 4 | CE 5 | CE 6 | CE 7 |
|---|---|---|---|---|---|---|---|---|
| Content of compound 2 (mg) | | 8.5 | 17 | 34 | 85 | 170 | 340 | 85 |
| Mass of capsule shell (mg) | | 65 | 65 | 65 | 65 | 65 | 99 | |
| Mass ratio: compound 2/capsule shell | | 0.13 | 0.26 | 0.52 | 1.3 | 2.6 | 3.4 | |
| Dissolution rate at 60 minutes (%) | Initial | 101.0 | 100.9 | 99.5 | 100.5 | 102.4 | 101.1 | 84.4 |
| | After storage in an unsealed state, 40° C. and 75% RH for 1 month | 92.4 | 50.6 | 27.8 | 5.4 | 2.7 | 1.8 | 8.1 |

TABLE 2

| | | Dissolution rate (%) | | | | | | |
|---|---|---|---|---|---|---|---|---|
| Time of measurement (min) | | 0 | 5 | 10 | 15 | 30 | 45 | 60 |
| Example 6 | Initial | 0.0 | 0.0 | 0.5 | 18.6 | 85.6 | 99.3 | 100.2 |
| | After storage in an unsealed state, 40° C. and 75% RH for 1 month | 0.0 | 0.2 | 0.8 | 11.7 | 64.4 | 97.3 | 106.1 |
| Comparative Example 6 | Initial | 0.0 | 10.5 | 35.3 | 57.2 | 91.7 | 100.9 | 101.1 |
| | After storage in an unsealed state, 40° C. and 75% RH for 1 month | 0.0 | 0.1 | 0.3 | 0.3 | 0.5 | 1.3 | 1.8 | more of compound 2 had an average dissolution rate of less than 10% even at 60 minutes after initiation of the test.

Example 8

796 g of compound 2, a phosphonooxymethyl derivative of ravuconazole and 4 g of magnesium stearate (produced by Mallinckrodt) were mixed. The resulting mixture was weighed at 172 mg in a hypromellose capsule shell (VcapsPlus®, size 2, produced by CAPSUGEL) to obtain a capsule formulation comprising 171 mg of compound 2 per capsule shell.

Example 9

794.4 g of compound 2, a phosphonooxymethyl derivative of ravuconazole, 1.6 g of magnesium oxide (produced by Kyowa Chemical Industry Co., Ltd.) and 4 g of magnesium stearate (produced by Mallinckrodt) were mixed. The resulting mixture was weighed at 172 mg in a hypromellose capsule shell (VcapsPlus®, size 2, produced by CAPSU-GEL) to obtain a capsule formulation comprising 171 mg of compound 2 per capsule shell.

Example 10

792 g of compound 2, a phosphonooxymethyl derivative of ravuconazole, 4 g of magnesium oxide (produced by Kyowa Chemical Industry Co., Ltd.) and 4 g of magnesium stearate (produced by Mallinckrodt) were mixed. The resulting mixture was weighed at 173 mg in a hypromellose capsule shell (VcapsPlus®, size 2, produced by CAPSU-GEL) to obtain a capsule formulation comprising 171 mg of compound 2 per capsule shell.

Example 11

788 g of compound 2, a phosphonooxymethyl derivative of ravuconazole, 8 g of magnesium oxide (produced by Kyowa Chemical Industry Co., Ltd.) and 4 g of magnesium stearate (produced by Mallinckrodt) were mixed. The resulting mixture was weighed at 174 mg in a hypromellose capsule shell (VcapsPlus®, size 2, produced by CAPSU-GEL) to obtain a capsule formulation comprising 171 mg of compound 2 per capsule shell.

Example 12

148.05 g of compound 2, a phosphonooxymethyl derivative of ravuconazole, 0.75 g of magnesium oxide (produced by Kyowa Chemical Industry Co., Ltd.) and 1.2 g of magnesium stearate (produced by Mallinckrodt) were mixed. The resulting mixture was weighed at 173 mg in a hypromellose capsule shell (VcapsPlus®, size 3, produced by CAPSUGEL) to obtain a capsule formulation comprising 171 mg of compound 2 per capsule shell.

Example 13

147.75 g of compound 2, a phosphonooxymethyl derivative of ravuconazole, 0.75 g of magnesium oxide (produced by Kyowa Chemical Industry Co., Ltd.) and 1.5 g of magnesium stearate (produced by Mallinckrodt) were mixed. The resulting mixture was weighed at 174 mg in a hypromellose capsule shell (VcapsPlus®, size 2, produced by CAPSUGEL) to obtain a capsule formulation comprising 171 mg of compound 2 per capsule shell.

Test Example 2

The hypromellose capsule formulation obtained in Example 12 was used as a sample. The sample was stored in an unsealed state in the same manner as Test Example 1 and the samples before and after the storage were assessed for dissolution behavior in the phosphate buffer, pH 6.8.

The average dissolution rate at 60 minutes after initiation of the test (dissolution rate at 60 minutes) for the samples before and after the storage is shown in Table 3. The dissolution rate shown in Table is the average dissolution rate of three samples.

TABLE 3

| | | Example 12 |
|---|---|---|
| Content of compound 2 (mg) | | 171 |
| Mass of capsule shell (mg) | | 47 |
| Mass ratio: compound 2/capsule shell | | 3.6 |
| Dissolution rate at 60 minutes (%) | Initial | 100.7 |
| | After storage in an unsealed state, 40° C. and 75% RH for 1 month | 98.1 |

The average dissolution rate of the samples of Example 12 which were stored at 40° C. did not drop compared to the initial value.

INDUSTRIAL APPLICABILITY

According to the present invention, the capsule formulation comprising a phosphonooxymethyl derivative of ravuconazole can be produced. The capsule formulation of the present invention suppresses delay in dissolution due to storage regardless of the encapsulated amount of the phosphonooxymethyl derivative of ravuconazole and therefore has an industrial applicability in the medical field.

I claim:
1. A capsule formulation comprising:
   an encapsulated material comprising {[(1R,2R)-2-[4-(4-cyanophenyl)-1,3-thiazol-2-yl]-1-(2,4-difluorophenyl)-1-(1H-1,2,4-triazol-1-ylmethyl)propyl]oxy}methyl dihydrogen phosphate or a pharmacologically acceptable salt thereof, or a solvate of any of the foregoing; and
   a capsule shell formed with a capsule shell base comprising starch, pullulan, polyvinyl alcohol or hypromellose,
   wherein the mass ratio of the {[(1R,2R)-2-[4-(4-cyanophenyl)-1,3-thiazol-2-yl]-1-(2,4-difluorophenyl)-1-(1H-1,2,4-triazol-1-ylmethyl)propyl]oxy}methyl dihydrogen phosphate or a pharmacologically acceptable salt thereof, or a solvate of any of the foregoing, based on the capsule shell is 0.27 or more.
2. The capsule formulation according to claim 1, wherein the capsule shell is formed with a capsule shell base comprising pullulan or hypromellose.
3. The capsule formulation according to claim 1, wherein the capsule shell is formed with a capsule shell base comprising hypromellose.
4. The capsule formulation according to claim 1, wherein the {[(1R,2R)-2-[4-(4-cyanophenyl)-1,3-thiazol-2-yl]-1-(2,4-difluorophenyl)-1-(1H-1,2,4-triazol-1-ylmethyl)propyl]oxy}methyl dihydrogen phosphate or the pharmacologically acceptable salt thereof, or the solvate of any of the foregoing is L-lysine-{[(1R,2R)-2[4-(4-cyanophenyl)-1,3-thiazol-2- yl]-1-(2,4-difluorophenyl)-1-(1H-1,2,4-triazol-1-ylmethyl)propyl]oxy}methyl dihydrogen phosphate-ethanol (1/1/1).

5. The capsule formulation according to claim 1, wherein the encapsulated material further comprises magnesium oxide.

6. A method for suppressing delay in dissolution of a capsule formulation comprising the compound {[(1R,2R)-2-[4-(4-cyanophenyl)-1,3-thiazol-2-yl]-1-(2,4-difluorophenyl)-1-(1H-1,2,4-triazol-1-ylmethyl)propyl]oxy}methyl dihydrogen phosphate, or a pharmacologically acceptable salt thereof, or a solvate of any of the foregoing, wherein the method comprises encapsulating the compound in a capsule shell formed with a capsule shell base comprising starch, pullulan, polyvinyl alcohol or hypromellose,
wherein the mass ratio of the {[(1R,2R)-2-[4-(4-cyanophenyl)-1,3-thiazol-2-yl]-1-(2,4-difluorophenyl)-1-(1H-1,2,4-triazol-1-ylmethyl)propyl]oxy}methyl dihydrogen phosphate or a pharmacologically acceptable salt thereof, or a solvate of any of the foregoing, based on the capsule shell is 0.27 or more.

7. The capsule formulation according to claim 1, wherein the mass ratio of the {[(1R,2R)-2-[4-(4-cyanophenyl)-1,3-thiazol-2-yl]-1-(2,4-difluorophenyl)-1-(1H-1,2,4-triazol-1-ylmethyl)propyl]oxy}methyl dihydrogen phosphate or a pharmacologically acceptable salt thereof, or a solvate of any of the foregoing, based on the capsule shell is 0.27 to 10.

8. The capsule formulation according to claim 1, wherein the mass of the {[(1R,2R)-2-[4-(4-cyanophenyl)-1,3-thiazol-2-yl]-1-(2,4-difluorophenyl)-1-(1H-1,2,4-triazol-1-ylmethyl)propyl]oxy}methyl dihydrogen phosphate or a pharmacologically acceptable salt thereof, or a solvate of any of the foregoing, contained in the capsule shell is 17 mg or more.

9. The capsule formulation according to claim 1, wherein the average dissolution rate of the {[(1R,2R)-2-[4-(4-cyanophenyl)-1,3-thiazol-2-yl]-1-(2,4-difluorophenyl)-1-(1H-1,2,4-triazol-1-ylmethyl)propyl]oxy}methyl dihydrogen phosphate or a pharmacologically acceptable salt thereof, or a solvate of any of the foregoing, at 60 minutes after initiation of the Dissolution Test according to the Japanese Pharmacopoeia 16$^{th}$ edition is 60% or more after storage in an unsealed state under the conditions of 40° C. and 75% relative humidity for 1 month.

10. The capsule formulation according to claim 1, wherein the average dissolution rate of the {[(1R,2R)-2-[4-(4-cyanophenyl)-1,3-thiazol-2-yl]-1-(2,4-difluorophenyl)-1-(1H-1,2,4-triazol-1-ylmethyl)propyl]oxy}methyl dihydrogen phosphate or a pharmacologically acceptable salt thereof, or a solvate of any of the foregoing, at 60 minutes after initiation of the Dissolution Test according to the Japanese Pharmacopoeia 16$^{th}$ edition is 85% or more after storage in an unsealed state under the conditions of 40° C. and 75% relative humidity for 1 month.

* * * * *

UNITED STATES PATENT AND TRADEMARK OFFICE
CERTIFICATE OF CORRECTION

PATENT NO. : 9,981,040 B2  
APPLICATION NO. : 14/390854  
DATED : May 29, 2018  
INVENTOR(S) : Yosuke Ueki Page 1 of 1

It is certified that error appears in the above-identified patent and that said Letters Patent is hereby corrected as shown below:

On the Title Page

In Item "(*) Notice", delete "0 days. days." and insert -- "0 days." --.

In the Claims

Column 16
Claim 4, Line 67, delete "L-lysine-{[(1*R*,2*R*)-2[4-(4-cyanophenyl)-1,3-thiazol-2-yl]-1-(2,4-difluorophenyl)-1-(1*H*-1,2,4-triazol-1-ylmethyl)propyl]oxy}methyl dihydrogen phosphate-ethanol (1/1/1)" and insert -- L-lysine-{[(1*R*,2*R*)-2-[4-(4-cyanophenyl)-1,3-thiazol-2-yl]-1-(2,4-difluorophenyl)-1-(1*H*-1,2,4-triazol-1-ylmethyl)propyl]oxy}methyl dihydrogen phosphate-ethanol (1/1/1) --.

Column 17
Claim 6, Line 7, delete "{[(1*R*,2*R*)-2[4-(4-cyanophenyl)-1,3-thiazol-2-yl]-1-(2,4-difluorophenyl)-1-(1*H*-1,2,4-triazol-1-ylmethyl)propyl]oxy}methyl dihydrogen phosphate" and insert -- {[(1*R*,2*R*)-2-[4-(4-cyanophenyl)-1,3-thiazol-2-yl]-1-(2,4-difluorophenyl)-1-(1*H*-1,2,4-triazol-1-ylmethyl)propyl]oxy}methyl dihydrogen phosphate --.

Signed and Sealed this  
Sixth Day of November, 2018

Andrei Iancu  
*Director of the United States Patent and Trademark Office*